United States Patent [19]

Anderson

[11] Patent Number: 5,069,203
[45] Date of Patent: Dec. 3, 1991

[54] SOFT HAND AND WRIST SPLINT

[76] Inventor: Janet P. Anderson, 21052 Winfield Rd., Topanga, Calif. 90290

[21] Appl. No.: 328,522

[22] Filed: Mar. 23, 1989

[51] Int. Cl.$^5$ ............................................. A61F 5/04
[52] U.S. Cl. ................................. 128/87 R; 128/87 A
[58] Field of Search ..................... 128/77, 87 A, 87 R, 128/165, 878, 879; 2/16, 20, 162; 273/54 B

[56] References Cited

U.S. PATENT DOCUMENTS

| | | | |
|---|---|---|---|
| 1,369,810 | 3/1921 | Hinze | 2/158 |
| 3,066,306 | 12/1962 | Thomas | 2/20 |
| 3,238,939 | 3/1966 | Stubbs | 2/16 |
| 3,496,573 | 2/1970 | Kuchar et al. | 2/16 |
| 3,533,407 | 10/1970 | Smith | 2/16 |
| 3,779,550 | 12/1973 | Benoun et al. | 128/89 R |
| 4,657,251 | 4/1987 | Larsen | 273/54 B |
| 4,716,892 | 1/1988 | Brunswick | 128/87 R |

Primary Examiner—Robert A. Hafer
Assistant Examiner—Charles H. Sam
Attorney, Agent, or Firm—Ladas & Parry

[57] ABSTRACT

A soft hand or hand and wrist splint for controlling and reducing hand and/or hand and wrist flexion contractures. The splint has a soft flexible body member such as polyurethane foam having a density of 1.1 to 2.0 pounds per cubic foot and an indentation load deflection on the order of 33 for a medium firm foam. The body member is sized so that its length extends from the fingertips to a region intermediate the thumb and the wrist or, if desired, to a region intermediate the wrist and the elbow depending upon whether just metacarpal flexion contratures are to be controlled or metacarpal and wrist flexion contractures are to be controlled, respectively. The body member is preferably covered with a soft stretch material such as a stretch terry cloth. A plurality of strap means are positionable over the body member and, if desired, may be secured or coupled to the terry cloth covering. The body member with the covering is adapted to be wrapped around the user's hand and/or hand, wrist and portion of the forearm area depending upon whether metacarpal flexion contractures or metacarpal and wrist flexion contractures are to be controlled. An aperture is provide through the body member and through the covering to allow the thumb of the user to extend therethrough in order to maintain thumb abduction. The straps are preferably adjustable in length so that varying degrees of compression of the body member upon the user may be made tightening or loosening the straps. Additionally, if desired, the density of the foam of the body member may be increased in certain preselected regions to provide greater resistance to metacarpal or metacarpal and wrist flexion contractures.

19 Claims, 2 Drawing Sheets

SOFT HAND AND WRIST SPLINT

BACKGROUND OF THE INVENTION

1. Field of the Invention

This invention relates to the splint art and more particularly to an improved soft splint which may be applied to a user's hand and/or hand and wrist for reduction of metacarpal flexion contractures and/or metacarpal and wrist flexion contractures.

2. Description of the Prior Art

In many applications it is desirable to reduce undesired hand and/or hand and wrist flexion contractures. It has been found, for example, that in many areas of treatment there is undesirable metacarpal and/or metacarpal and wrist flexion contractures which should be reduced and or prevented in order to allow the person suffering from such a disability to recover. In the past, comparatively rigid splints have been applied to the hand such as in the metacarpal area or to the hand and wrist to prevent metacarpal and/or metacarpal and wrist flexion contractures. It has been found that such metacarpal and/or metacarpal and wrist flexion contractures may occur after a head trauma, after cerebral vascular accidents, to persons suffering from cerebral palsy, after a person has come close to drowning, in certain post burn patients, after some hand surgeries, a person suffering from such diseases as multiple sclerosis, muscular dystrophy, arthritis, Parkinson's disease, or even just as a result of age. For purposes of explanation herein, it will be appreciated that metacarpal flexion contracture may be defined as the bending of the fingers from the metacarpophalangeal joint from an extended position towards the palm of the hand. Wrist flexion contractures are defined as bending of the wrist to move the hand towards the forearm. Both of these flexion contractures have a maximum range of approximately 90 degrees from the extended condition thereof.

The rigid splints as above identified and as heretofore utilized have had many disadvantages in that they did not provide an adjustability as to the amount of pressure that could be applied but, instead, provided only of course a rigid resistance to such contractures. Additionally, such rigid splints were often very uncomfortable to the user.

Additionally, it has been found that with the rigid splints thumb abduction could not be maintained while providing the desired benefits of the splint.

Therefore, there has long been a need for a soft hand splint for reducing and/or controlling hand and/or hand and wrist flexion contractures but which is not rigid, is comfortable to use, and in which the resistance thereof may be suitably varied as the user requires, and also that the splint maintains thumb abduction.

SUMMARY OF THE INVENTION

Accordingly, it is an object of the present invention to provide an improved hand and/or hand and wrist splint.

It is another object of the present invention to provide an improved hand and/or hand and wrist splint which is soft and comfortable for the user to wear.

It is another object of the present invention to provide an improved and/or hand and wrist splint that is soft and comfortable for the user to wear and which reduces hand and/or hand and wrist flexion contractures.

It is another object of the present invention to provide such an improved hand and wrist splint that can provide a varying degree of resistance to metacarpal flexion contractures or both metacarpal and wrist flexion contractures.

The above and other objects are achieved, according to a preferred embodiment of the present invention, by providing a soft hand splint for reducing hand and/or hand and wrist flexion contractures. The splint has a soft, flexible resilient body member such as a polyurethane foam of a soft to medium firm density which may be, for example, on the order of 1.1 to 2.0 pounds per cubic foot and an indentation load deflection on the order of 33 for a medium firm foam. The body member may be on the order of 1" to 2" thick. The length of the body member is selected to extend from regions adjacent the user's fingertips to regions intermediate the base of the thumb and the wrist, for splints providing a reduction in hand or metacarpal flexion contractures or, alternatively, the length may be selected so that it extends to a region between the wrist and the elbow of the user so that both metacarpal flexion contractures as well as wrist flexion contractures may be reduced. The width of the body member is selected so that the splint may be wrapped around the hand of the user. In preferred embodiments of the present invention such width may be selected so that the lateral edges of the body member are positioned in close proximity to each other when the splint is applied to the user. However, it will be appreciated, that the splint may also be configured so that it may be wrapped around the hand of the user such that the first edge overlaps the second edge (or vice-versa) if desired.

A soft covering such as a stretch terry cloth is applied over at least the outer surface and inner surface of the body member and, preferably, also extends completely over the lateral edges and the end edges of the body member so that the body member is fully contained within the stretch terry cloth covering.

A plurality of strap means may be utilized with the hand splint to apply the hand splint to the user in a wrapped around condition around the hand and/or the hand and wrist thereof and thus retain the hand splint in place. In some embodiments it may be preferable to use separate straps. That is, the straps may be separate from the splint itself. However, in preferred embodiments of the present invention, there are a plurality of straps in a spaced array and the straps have a first end coupled to the outer surface of the covering and the second end of the straps is remote from the first end. An adjustable length of the straps for securing the hand splint to the user with varying degrees of compression thereof may be achieved by having, for example, buckles on the straps, a Velcro type closure on the straps, an Aplix type closure or the like. Velcro type closures which may be defined as hook and loop closures provide a sanitary and fully adjustable releasable securing of the strap means for this application.

The body member and the covering have walls defining an aperture therethrough and the walls are placed on the splint in regions adjacent the user's thumb. The aperture allows the user's thumb to project through the hand splint and thus the hand splint of the present invention maintains thumb abduction when applied to a user. This, of course, is very important to the patient so that the abduction of the thumb may be maintained while at the same time there is a reduction in the hand and/or hand and wrist flexion contractures.

In other embodiments of the present invention, additional reduction in metacarpal and/or metacarpal and wrist flexion contractures can be provided by providing preselected regions of the body member with a soft flexible resilient polyurethane foam having a greater density than the remainder of the body member. Such higher density of the foam in these regions provides greater resistance and therefore increased reduction of metacarpal and wrist flexion contractures when appropriately place.

BRIEF DESCRIPTION OF THE DRAWINGS

The above and other embodiments of the present invention may be more fully understood from the following detailed description taken together with the accompanying drawings wherein similar reference characters refer to similar elements throughout and in which.

DESCRIPTION OF THE PREFERRED EMBODIMENTS

The present invention of a soft hand splint which may be utilized to control or reduce metacarpal flexion contracture or, if desired, both metacarpal flexion contracture and wrist flexion contracture, or just wrist flexion contracture is illustrated in the accompanying drawings. The benefits of soft splints for reducing flexion contracture have been described, for example, in the publication "Developmental Medicine and Child Neurology", 1988, Number 30, pages 502–508 "Efficacy of Soft Splints in Reducing Severe Knee-Flexion Contractures" by Anderson, Snow, Dorey and Kabo. This article describes the use of a soft splint made of polyurethane foam in treating knee flexion contractures. However, the particular requirements of reducing metacarpal and/or wrist and metacarpal flexion contractures are significantly different than preventing knee flexion contractures. That is, the presence of the thumb and the requirement for maintaining thumb abduction requires a new type of a soft hand and/or hand and wrist splint.

Figure 1:
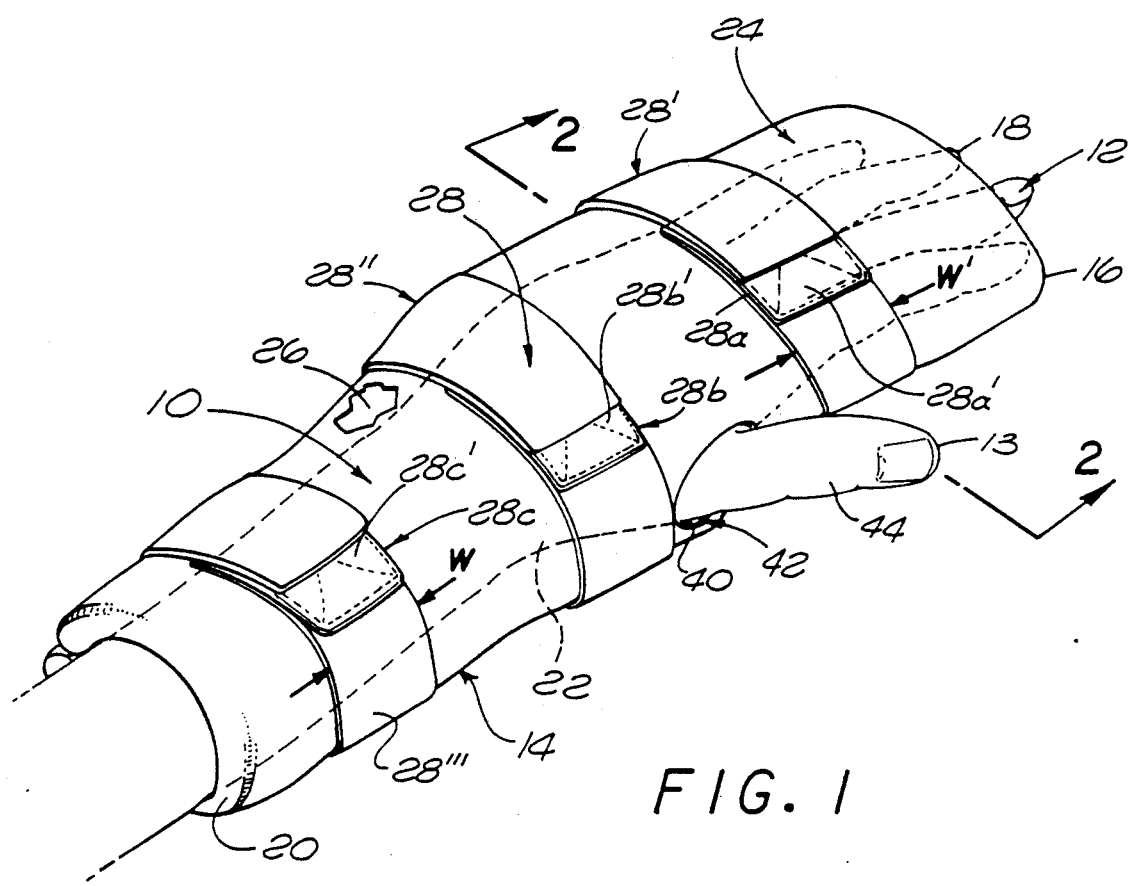
FIG. 1 illustrates a soft hand and wrist splint according to principals of the present invention.

Referring now to the drawings there is illustrated in FIG. 1 an embodiment generally designated 10 of the present invention of a soft hand and wrist splint as applied to a user 12 on the hand thereof generally designated 13. In the embodiment 10 the hand and wrist splint 14 has a first end 16 in regions adjacent the fingertips as illustrated at 18 of the user 12 and a second end generally designated 20 spaced by the preselected length of the splint 14 from the first end 16. In the embodiment 10 illustrated in FIG. 1 the hand splint is selected to provide, as described below in greater detail, a reduction of both metacarpal flexion contractures and wrist flexion contractures. Accordingly, the second end 20 extends past the wrist area generally designated at 22 to a region between the wrist area 22 and the elbow (not shown in FIG. 1) of the user 12. The hand splint 14 has an outer covering 24 and a body member 26. The body member 26 is preferably a soft flexible resilient material such as a polyurethane foam and may, for example, have a density on the order 1.1 to 2.0 pounds per cubic foot, and is a generally soft to medium firm polyurethane foam in preferred embodiments of the present invention. The indentation load deflection of the body member 26 is preferably on the order of 33 on a medium firm foam. It will be appreciated, of course, that the particular foam used for particular applications depends on the size and strength of the hand which is to be splinted to prevent the metacarpal flexion contractures and/or the metacarpal flexion contractures and wrist flexion contractures. That is, for small children and infants a lower density foam will be utilized whereas for larger and stronger people a higher density foam will be utilized or depending upon the degree of resistance required for particular applications. The person selecting the particular foam density will, of course, know the desired density for the particular person from experience in dealing with such applications.

The outer covering 24 is preferably a stretch terry cloth though, it will be appreciated, any desired type of outer covering having a similar type of one-way stretch characteristic may be utilized that is suitable for the purpose. It should be a soft and relatively easily cleanseable outer covering for obvious sanitary reasons. It has been found that one-way stretch materials utilized for the outer cover 24 provides the splint with the necessary properties for proper splint functioning. The one-way stretch, in preferred embodiments of the present invention, is in directions parallel to the ends 16 and 20.

The body member 26 with the covering 24 thereon is retained on the hand of the user 12 by a plurality of strap means generally designated 28 in a predetermined spaced array. The predetermined spaced array is preselected so that a first strap such as 28' is in the metacarpal region of the user 12 when the splint 14 is applied to the user, a second strap means 28" is in the regions of the wrist of the user 12 and a third strap means 28''' is between the wrist and the elbow of user 12. The tension of the strap means may be adjusted to provide any desired compression of the hand splint 14 as desired. In the embodiment 10 illustrated on FIG. 1 the strap means are secured to the outer covering 24 as indicated generally at 28a, 28b and 28c. The strap means 28 are preferably adjustable in length and, to achieve such adjustment, a hook and loop type of closure such as Velcro may be utilized as indicated at 28a', 28b' and 28c'. Thus, the strap means 28 has a predetermined length to permit the desired adjustability of compression as well as adjustability for different sizes of a user 12. Similarly, the strap means 28 have a preselected width indicated by W on FIG. 1 which, for example, may be on the order of 1" to 2" depending upon the size of the hand user 12.

It will be appreciated that the strap means 12 may be separate from the covering 24 and body member 26. That is, separate straps not secured to the splint may be utilized and such straps may have buckles or other type of closures, as described above, thereon for providing adjustable lengths for securing the hand splint 14 to the user 12. Such straps are not illustrated in FIG. 1.

The body member 26 has a preselected thickness which may, for example, be on the order of 1" to 2" depending on the particular user 12 for whom the hand splint 14 is require.

The strap 28' may be sized to cover any desired number of joints of the fingers as required. That is, the width W' of strap means 28' may be sufficient to adjust the metacarpophalangeal joints of the fingers and the proximal interphalangeal joints of the finger if desired or, alternatively, just the metacarpophalageal joint. This will depend of course upon the particular problems that are desired to be corrected for the particular user 12.

The strap 28" is positioned, preferably, over the wrist 22 of the user and the strap 28''' may be positioned, for example, between the wrist 22 and the elbow (not shown) of the user 12 by spacing the strap 28''' approximately 1½" from the second end 20.

The covering 24 and body member 26 each have walls generally designated 40 defining an aperture generally designated 42 through which the thumb 44 of the user 12 may project when the splint 14 is applied to the user 12. It has been found that this aperture 42 is very important in treating flexion contractures of the metacarpals and/or the flexion contractures of the wrist as it allows abduction of the thumb 44 to be maintained even though the splint 14 is in place. That is, some prior splints such as some hard splints did not allow the maintenance of thumb abduction when they were installed. Thus, the soft splint 14 of the present invention is more effective in treating the user 12 to provide reduction of metacarpal and/or metacarpal and wrist flexion contractures and yet still maintaining the thumb abduction throughout the use of the splint.

Figure 2:
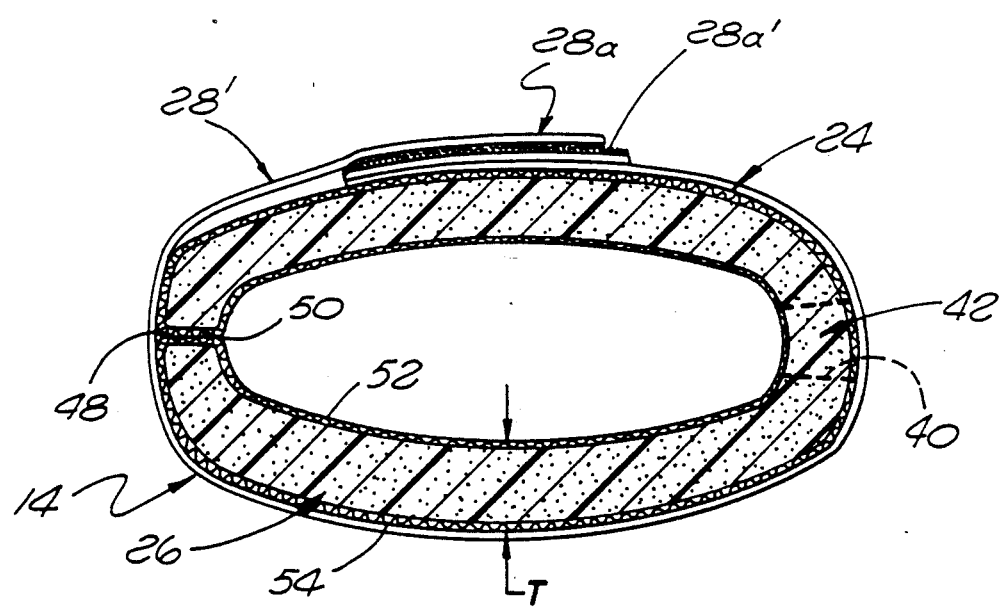
FIG. 2 is a sectional view along the line 2—2 of FIG. 1.

FIG. 2 is a sectional view along the line 2—2 of FIG. 1 in which the hand 13 of the user 12 has been omitted for clarity. The body member 26 has a thickness as noted above and as indicated on FIG. 2 by the letter T in the range of 1" to 2" depending upon the desired resistance to flexion contractures. The body member 26 has a first lateral edge 48 and a second lateral edge 50 which, when the splint 14 is applied to user 12 are adjacent to each other in opposed relationship. However, it will be appreciated, that in other embodiments of the present invention the first lateral edge 48 and regions of the splint 14 adjacent thereto may overlap the second lateral edge 50 and regions adjacent thereto depending upon the size of the hand 13 of the user 12. The body member 26 also has an inner surface 52 and an outer surface 54 which, in the preferred embodiment to the present invention are both covered by the soft covering 24 as are the first end 16 and second end 20 of the soft splint 14.

Figure 3:
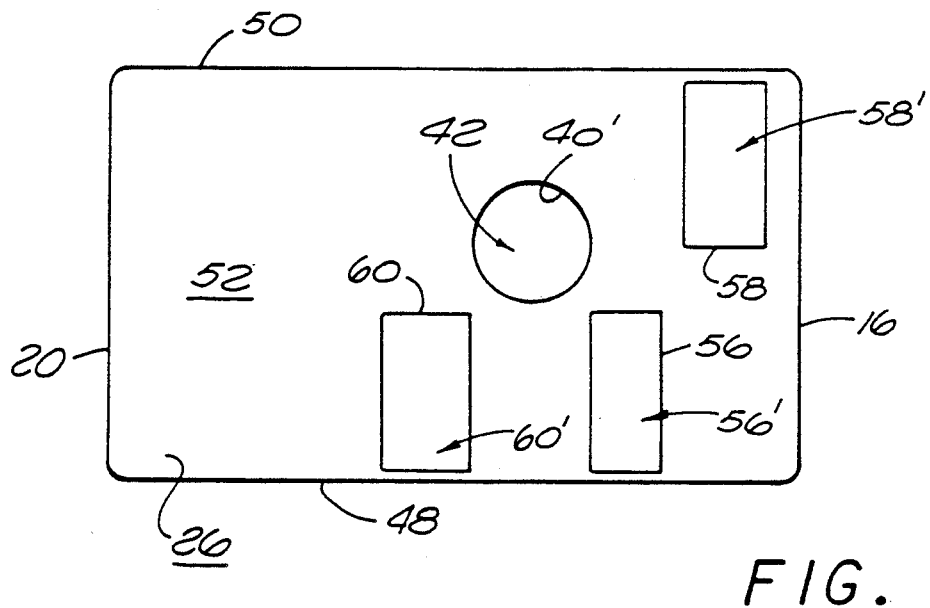
FIG. 3 and FIG. 4 are plan views of a hand splint according to the principles of the present invention.

Referring now to FIG. 3 there is illustrated a plan view of the body member 26 according to the principle of the present invention. As illustrated in FIG. 3 the inner surface 52 is shown and the walls 40' therein defining the thumb receiving aperture 42 are shown in regions adjacent the first end 16 thereof. In order to provide even greater resistance to metacarpal flexion contracture, certain regions of the body member 26 may be provided with a greater density of polyurethane foam. Thus, in the regions generally designated 56 and 58 there may be provided polyurethane foam generally designated 56' and 58' that has a greater density than the density of the remaining portions of the body member 26 to provide greater resistance to metacarpal flexion contractures. Similarly, there may be provided in regions generally designated 60 an increased foam density generally designated 60' to provide greater resistance to wrist flexion contractures.

Figure 4:
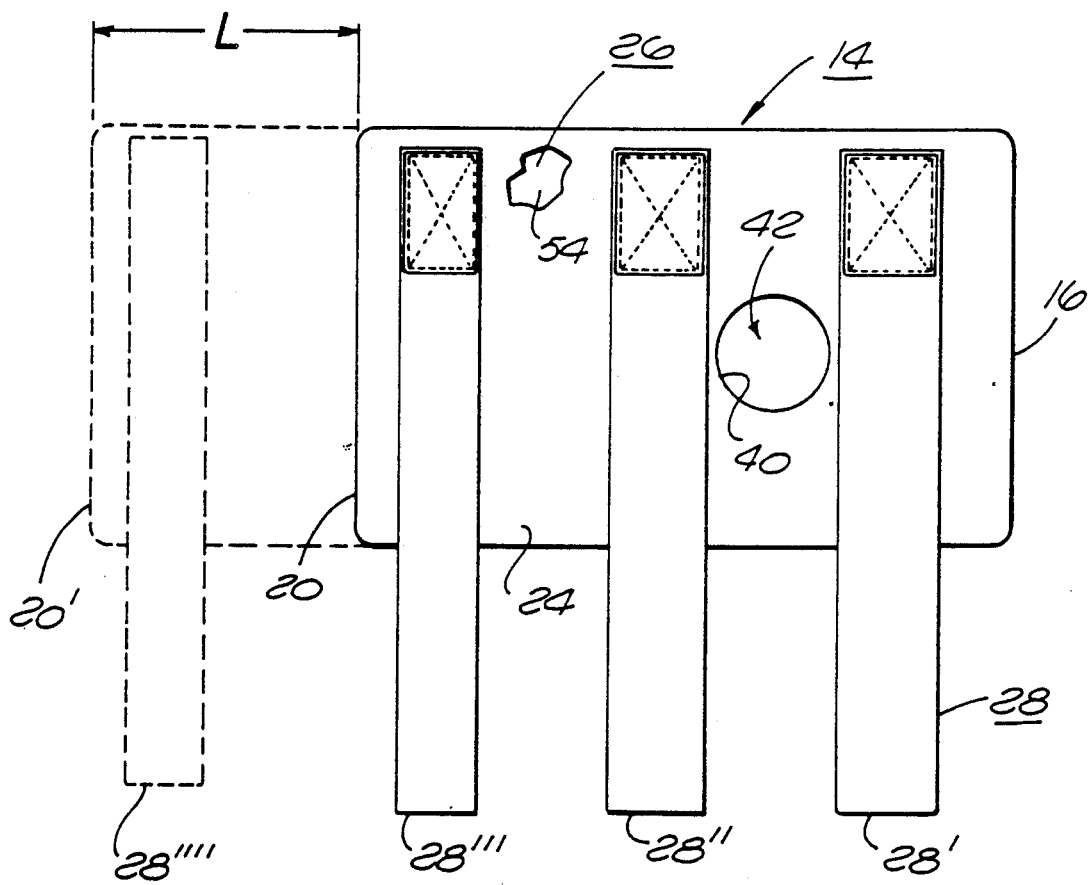

Referring now to FIG. 4 there is illustrated a plan view of the body member 26 showing the outer surface 54. The covering of 24 is shown as installed thereover and the strap means 28 such as strap means 28', 28" and 28''' are also shown as illustrated in the embodiment 10 shown on FIG. 1. That is, the strap means 28 are coupled to the covering 24. It will be appreciated that additional length as indicated by the letter L as well as an additional strap means such as strap means 28'''' may be provided for desired applications to provide the second end 20' spaced at a greater distance from the first end 16 of the soft splint 14. The thumb receiving aperture 42 defined by the first walls 40 through the covering 24 and body member 26 are also shown in FIG. 4.

This concludes the description of the preferred embodiments of the present invention. It will be appreciated that the soft splint of the present invention is adaptable for use to provide resistance to metacarpal flexion contracture as well as both metacarpal flexion contracture and wrist flexion contracture. The soft splint is comfortable to wear and thus may be utilized, for example, at night when the user is sleeping and it has provided high effectiveness when so used since the user is relaxed when sleeping. Further, there is a high degree of utility in the soft splint in that it may be completely adjustable for varying degrees of compression and therefore varying degrees of resistance to such flexion contractures and the resistance of the soft splint continues to be applied even as mobility of the particular joints is gained. Importantly, thumb abduction is maintained during utilization of the soft splint according to the principles of the present invention.

Accordingly, the following claims are intended to cover all variations and adaptations of the present invention falling within the true scope and spirit thereof.

What is claimed is:

1. A hand splint of the type adapted to reduce hand and wrist flexion contractures and comprising, in combination:

a soft, flexible resilient body member having a first preselected indentation load deflection and at least a first preselected density in predetermined regions thereof, and further having a predetermined length and predetermined width, said predetermined length comprising a length extending from regions adjacent a user's fingertips a preselected distance towards such users elbow, said predetermined width comprising a width sufficient to wrap said body member around the hand of the user, and said body member in close proximity to the user's fingers and wrist for exerting a predetermined resilient force thereon for reducing flexion contractures of said fingers and wrist, and said body member further having:

an outer surface;

an inner surface, and a preselected thickness between said outer surface and said inner surface;

a first end positionable in regions adjacent a user's fingertips;

a second end spaced said preselected length from said first end;

a first lateral edge; and a second lateral edge spaced said preselected width from said first lateral edge, and said first lateral edge in regions adjacent said second lateral edge for the condition of said body member applied to a user's hand;

a one-way stretch soft covering extending at least over said outer surface and said inner surface of said body member;

a plurality of strap means on said soft covering and overlying said outer surface of said body member in a predetermined spaced array and extending therearound in directions transverse to said first and second lateral edges for retaining the hand splint on the user's hand, and said plurality of strap means having a predetermined strap width;

securing means cooperating with said strap means to retain said hand splint on the user;

said body member having first walls defining a thumb receiving aperture therethrough in a predetermined location thereof in regions adjacent said first end of said body member for allowing a user's thumb to project through said body member from said inner surface to said outer surface for the condition of said body member applied to a user;

said covering has second walls defining an aperture therethrough, and said second walls in registerable alignment with said first walls to allow the user's thumb to project therethrough; and free of rigid support members preventing hand or wrist flexion contractures.

2. The arrangement defined in claim 1 wherein:
said strap means further comprises a first end coupled to said covering, and a second end spaced from said first end by a preselected strap length.

3. The arrangement defined in claim 2 wherein:
said securing means further comprises a releasable securing means.

4. The arrangement defined in claim 3 wherein:
said releasable securing means comprises a hook and loop means.

5. The arrangement defined in claim 1 wherein:
said body member has a second preselected density greater than said first preselected density in first predetermined regions thereof for additional reduction of metacarpal flexion contractures.

6. The arrangement defined in claim 1 wherein:
said body member has a second preselected density in second predetermined regions for reduction of wrist flexion contractures.

7. The arrangement defined in claim 1 wherein:
said preselected length extends from regions adjacent the user's fingertips to regions intermediate the user's wrist and the user's elbow.

8. The arrangement defined in claim 1 wherein:
said predetermined length extends from regions adjacent the user's fingertips to regions intermediate the user's thumb and the user's wrist.

9. The arrangement defined in claim 1 wherein:
said body member is fabricated from a soft to medium firm polyurethane foam;
said predetermined thickness is in the range of 1.0" to 2.0";
said first predetermined density is in the range of 1.1 to 2.0 pounds per cubic foot;
said first predetermined indentation load deflection is on the order of 33 on medium firm foam;
said predetermined strap width is in the range of 1.0" to 2.0"; and
said soft covering is fabricated from one-way stretch terry cloth.

10. The arrangement defined in claim 9 wherein:
said stretch terry cloth covering extends over said first end, said second end, said first lateral edge, and said second lateral edge; and
the direction of said one-way stretch is substantially parallel to the first and second ends.

11. The arrangement defined in claim 10 wherein:
said strap means further comprises a first end secured to said covering, and a second end spaced a preselected strap length therefrom;
said securing means further comprises a releasable securing means, and said releasable securing means comprises a hook and loop means.

12. The arrangement defined in claim 11 wherein:
said preselected length extends from regions adjacent the user's fingertips to regions intermediate the user's wrist and the user's elbow;
said plurality of strap means comprises at least three.

13. The arrangement defined in claim 11 wherein:
said predetermined length extends from regions adjacent the user's fingertips to regions intermediate the user's thumb and the user's wrist; and
said plurality of strap means comprises at least two.

14. The arrangement defined in claim 12 wherein:
a first of said plurality of straps is positioned over the metacarpals of the user for the condition of a body member applied to the user; and
a second of said plurality of straps is positioned over the wrist for the condition of the body member applied through a user; and
a third of said plurality of strap means is positioned intermediate the wrist and elbow of the user for the condition of the body member applied to a user.

15. The arrangement defined in claim 13 wherein:
a first of said plurality of straps is positioned over the metacarpals of the user for the condition of the body member applied to a user;
a second of said plurality of straps is positioned in regions adjacent the wrist of the user for the condition of the body member applied to a user.

16. The arrangement defined in claim 14 wherein:
said body member has a second preselected density greater than said first preselected density in first predetermined regions thereof for additional reduction of metacarpal flexion contractures.

17. The arrangement defined in claim 16 wherein:
said body member has a second preselected density in second predetermined regions for reduction in wrist flexion contractures.

18. The arrangement defined in claim 15 wherein:
said body member has a second preselected density greater than said first preselected density in first predetermined regions thereof for additional reduction of metacarpal flexion contractures.

19. The arrangement defined in claim 5 and further comprising:
said body member has said second preselected density in second predetermined regions for reduction of wrist flexion contractures.

* * * * *